(12) United States Patent
Hwang et al.

(10) Patent No.: US 11,589,960 B2
(45) Date of Patent: Feb. 28, 2023

(54) CUSTOMIZED ALVEOLAR BONE TISSUE AND METHOD OF FORMING THE SAME

(71) Applicant: IUCF-HYU (INDUSTRY-UNIVERSITY COOPERATION FOUNDATION HANYANG UNIVERSITY), Seoul (KR)

(72) Inventors: Kyung-Gyun Hwang, Seoul (KR); Hyunjae Cho, Seoul (KR); Jaeyun Jeon, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 837 days.

(21) Appl. No.: 15/870,303

(22) Filed: Jan. 12, 2018

(65) Prior Publication Data
US 2018/0132976 A1     May 17, 2018

Related U.S. Application Data

(63) Continuation of application No. PCT/KR2016/007630, filed on Jul. 13, 2016.

(30) Foreign Application Priority Data

Jul. 13, 2015 (KR) .......... 10-2015-0099164
Mar. 22, 2016 (KR) .......... 10-2016-0033880
Mar. 22, 2016 (KR) .......... 10-2016-0033915

(51) Int. Cl.
*A61C 8/00* (2006.01)
*A61B 6/14* (2006.01)
(Continued)

(52) U.S. Cl.
CPC .......... *A61C 8/0006* (2013.01); *A61B 6/032* (2013.01); *A61B 6/14* (2013.01); *A61C 8/008* (2013.01);
(Continued)

(58) Field of Classification Search
CPC ... A61C 8/0006; A61C 8/0018; A61C 8/0031; A61C 8/008; A61C 9/004;
(Continued)

(56) References Cited

U.S. PATENT DOCUMENTS 5,093,179 A * 3/1992 Scantlebury ......... A61C 8/0006
                                                    428/105
5,324,294 A * 6/1994 Elia ........................ A61L 27/12
                                                    606/76
(Continued)

FOREIGN PATENT DOCUMENTS

EP  0 574 091 A2   12/1993
JP  2012-516308 A   7/2012
(Continued)

OTHER PUBLICATIONS

International Search Report for PCT/KR2016/007630 dated Oct. 12, 2016 [PCT/ISA/210].

*Primary Examiner* — Edward Moran
*Assistant Examiner* — Matthew P Saunders
(74) *Attorney, Agent, or Firm* — Sughrue Mion, PLLC (57) ABSTRACT

Provided is a method of forming a customized alveolar bone tissue. The method includes obtaining first data having image information corresponding to an original alveolar bone of an alveolar bone defect, obtaining second data having image information on a defective portion of the alveolar bone defect, calculating third data having image information on a barrier membrane covering the alveolar bone defect by using the first data and the second data, and
(Continued)

forming a barrier membrane artificial tissue corresponding to the barrier membrane by using the third data.

4 Claims, 10 Drawing Sheets

(51) Int. Cl.
  *A61C 13/00* (2006.01)
  *A61C 8/02* (2006.01)
  *A61B 6/03* (2006.01)
  *A61C 9/00* (2006.01)
  *A61C 13/20* (2006.01)
  *A61C 13/225* (2006.01)

(52) U.S. Cl.
  CPC .......... *A61C 8/0012* (2013.01); *A61C 8/0018* (2013.01); *A61C 8/0031* (2013.01); *A61C 9/004* (2013.01); *A61C 13/0004* (2013.01); *A61C 13/0019* (2013.01); *A61C 13/20* (2013.01); *A61C 13/225* (2013.01)

(58) Field of Classification Search
  CPC . A61C 13/0004; A61C 13/0019; A61C 13/20; A61C 13/225; A61B 6/032; A61B 6/14; B29C 37/0081; A61F 2/28; A61F 2002/2817; B29K 2033/12
  See application file for complete search history.

(56) References Cited

U.S. PATENT DOCUMENTS

| | | | | |
|---|---|---|---|---|
| 5,496,371 A * | 3/1996 | Eppley | ................ | A61F 2/30721 623/17.18 |
| 5,824,088 A * | 10/1998 | Kirsch | .................... | A61L 31/10 424/423 |
| 6,328,765 B1 * | 12/2001 | Hardwick | ............. | A61F 2/2803 623/23.58 |
| 6,402,518 B1 * | 6/2002 | Ashman | ............... | A61C 8/0006 623/908 |
| 6,409,764 B1 * | 6/2002 | White | ..................... | A61L 27/54 623/16.11 |
| 7,172,422 B1 * | 2/2007 | Essiger | .............. | A61B 17/8038 433/172 |
| 8,343,225 B2 * | 1/2013 | Linares | ................. | A61F 2/2875 623/17.19 |
| 8,388,881 B2 * | 3/2013 | Giori | ....................... | B29C 70/76 264/250 |
| 8,974,535 B2 * | 3/2015 | Antonyshyn | ......... | B29C 51/428 623/17.18 |
| 9,616,153 B2 * | 4/2017 | McKay | .................. | A61L 27/40 |
| 9,861,482 B2 * | 1/2018 | Boiangiu | ............... | A61C 1/084 |
| 10,512,546 B2 * | 12/2019 | Kamer | ................... | A61B 34/10 |
| 2002/0055698 A1 * | 5/2002 | Ashman | ............... | A61C 8/0006 602/41 |
| 2002/0160175 A1 * | 10/2002 | Pirhonen | ................ | A61L 27/54 428/297.4 |
| 2003/0109784 A1 * | 6/2003 | Loh | ........................ | B33Y 50/00 600/427 |
| 2004/0024466 A1 * | 2/2004 | Heerklotz | ............. | A61F 2/2803 623/17.17 |
| 2006/0276875 A1 * | 12/2006 | Stinson | ................... | A61F 2/915 623/1.15 |
| 2007/0269769 A1 * | 11/2007 | Marchesi | ............. | A61L 31/146 433/215 |
| 2009/0181347 A1 * | 7/2009 | Lin | ....................... | A61C 8/0006 433/215 |
| 2010/0215718 A1 * | 8/2010 | Swords | ................. | A61L 27/227 424/423 |
| 2012/0045735 A1 * | 2/2012 | Drapeau | .............. | A61C 8/0006 433/172 |
| 2012/0046914 A1 | 2/2012 | Gao | | |
| 2012/0244498 A1 * | 9/2012 | Hall | ...................... | A61F 2/2846 433/201.1 |
| 2012/0310364 A1 * | 12/2012 | Li | ........................ | B29C 33/3842 623/23.55 |
| 2013/0090742 A1 * | 4/2013 | Boiangiu | .............. | A61F 2/2846 623/23.61 |
| 2013/0226534 A1 * | 8/2013 | Fisker | ..................... | G06F 30/00 703/1 |
| 2013/0288200 A1 * | 10/2013 | Battula | .................. | A61C 8/008 433/173 |
| 2014/0038132 A1 * | 2/2014 | Willis | ...................... | A61K 6/84 433/173 |
| 2014/0099601 A1 * | 4/2014 | Bassett | ................. | A61C 8/0006 433/173 |
| 2014/0349251 A1 * | 11/2014 | Moon | ................... | A61C 8/0006 433/174 |
| 2015/0054195 A1 * | 2/2015 | Greyf | ........................ | A61F 2/28 264/250 |
| 2015/0198943 A1 * | 7/2015 | Kotlus | .................... | G06T 19/20 623/17.16 |
| 2017/0014169 A1 * | 1/2017 | Dean | .................. | A61B 17/8071 |
| 2017/0360565 A1 * | 12/2017 | Seiler | ................... | A61C 8/0006 |
| 2018/0228513 A1 * | 8/2018 | Lizarazo Rozo | ...... | A61B 17/58 |
| 2020/0315753 A1 * | 10/2020 | Jo | ....................... | A61C 13/0019 |

FOREIGN PATENT DOCUMENTS

| | | |
|---|---|---|
| JP | 5463496 B2 | 4/2014 |
| KR | 10-0795645 B1 | 1/2008 |
| KR | 10-2008-0050982 A | 6/2008 |
| KR | 10-2011-0049884 A | 5/2011 |
| KR | 10-1181877 B1 | 9/2012 |
| KR | 10-2014-0055712 A | 5/2014 |

* cited by examiner

CUSTOMIZED ALVEOLAR BONE TISSUE AND METHOD OF FORMING THE SAME

CROSS-REFERENCE TO RELATED APPLICATION

This application is a continuation of pending International Application No. PCT/KR2016/007630, which was filed on Jul. 13, 2016 and claims priority to Korean Patent Application Nos. 10-2015-0099164, 10-2016-0033880 and 10-2016-0033915, filed on Jul. 13, 2015, Mar. 22, 2016 and Mar. 22, 2016, in the Korean Intellectual Property Office, the disclosures of which are hereby incorporated by reference in their entireties.

BACKGROUND

1. Field

Embodiments of the inventive concepts relate to a customized alveolar bone tissue and a method of forming the same and, more particularly, to a customized alveolar bone tissue applicable to a reconstruction treatment for an alveolar bone defect and a method of forming the same.

2. Description of the Related Art

An alveolar bone means a bone that has holes, in which teeth are embedded, in the upper or lower jaw. The alveolar bone is an essential anatomical element in the long-term stability and function of implants or teeth. The alveolar bone may be lost due to an injury caused by an accident, inflammation caused by gum infection (periodontitis), or bacterial plaque accumulated in teeth.

When the alveolar bone is defective or lost, it may be difficult to restore the anatomical and functional teeth shape by a method using a prosthetic procedure. In addition, an aesthetic problem may be caused in anterior teeth, and an oral hygiene problem may be caused in posterior teeth. In addition, it may not be easy to perform an implant surgery on a defective portion of the alveolar bone.

Various methods of regenerating the defective portion of the alveolar bone are being studied to solve the above problems. For example, methods of regenerating the alveolar bone by differentiating bone marrow-derived stem cells and teeth-related adult stem cells into osteoclasts have been studied. In addition, methods of grafting an autogenous bone, an allogeneic bone, a heterogeneous bone, a synthetic bone have been studied to assist the alveolar bone to be regenerated.

In a general alveolar bone graft, an alveolar bone condition before a tooth is lost may not be considered and a dental implant may be placed in a condition in which the tooth is lost. This alveolar bone graft may not completely perform functional and aesthetic reconstruction similar to a condition in which a tooth and an alveolar bone are healthy.

In addition, a conventional guide bone barrier membrane used in a bone graft using a barrier membrane at an alveolar bone defect may have a planar shape. Thus, when the conventional guide bone barrier membrane is applied to a patient, a reconstruction shape of an alveolar bone shape should be formed manually. As a result, an operation time may become longer and errors may easily occur in the operation.

Moreover, a customized titanium barrier membrane provided in a market may not consider characteristics of each patient and thus may not achieve functional and aesthetic reconstruction.

Furthermore, in the bone graft using the barrier membrane at the alveolar bone defect, the barrier membrane may be fixed using a metal screw nail (a block shape) or a suture with surrounding tissue. However, in this case, a surrounding bone tissue may be damaged, and soft tissue may be ruptured, and a time for which the barrier membrane is fixed may be greatly increased. In the method using the suture, the fixation may be unstable to cause deformation of an original shape.

SUMMARY

Embodiments of the inventive concepts may provide a customized alveolar bone tissue with high reliability and a method of forming the same.

Embodiments of the inventive concepts may also provide a customized alveolar bone tissue capable of reducing an operation time of an alveolar bone graft and a method of forming the same.

Embodiments of the inventive concepts may further provide a customized alveolar bone tissue capable of easily achieving functional and aesthetic restoration of a tooth and a method of forming the same.

Embodiments of the inventive concepts may further provide a customized alveolar bone tissue using three-dimensional (3D) printing and a method of forming the same.

In an aspect, a method of forming a customized alveolar bone tissue may include obtaining first data having image information corresponding to an original alveolar bone of an alveolar bone defect, obtaining second data having image information on a defective portion of the alveolar bone defect, calculating third data having image information on a barrier membrane covering the alveolar bone defect by using the first data and the second data, and forming a barrier membrane artificial tissue corresponding to the barrier membrane by using the third data.

In an aspect, a customized alveolar bone tissue shielding an alveolar bone loss region may include a cover portion covering a top of the alveolar bone loss region, and an adhesion portion extending from the cover portion and being adhered to an alveolar bone in a region adjacent to the alveolar bone loss region. The adhesion portion may be adhered to the alveolar bone by an adhesive.

In an aspect, a method of forming a customized alveolar bone tissue shielding an alveolar bone loss region may include obtaining image data on the alveolar bone loss region through a computerized tomography (CT) scan, forming a mold of the alveolar bone loss region from the image data, removing a region corresponding to the customized alveolar bone tissue from the mold, forming the customized alveolar bone tissue on the mold from which the region corresponding to the customized alveolar bone tissue is removed, and removing the mold from the customized alveolar bone tissue.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

Figure 1:
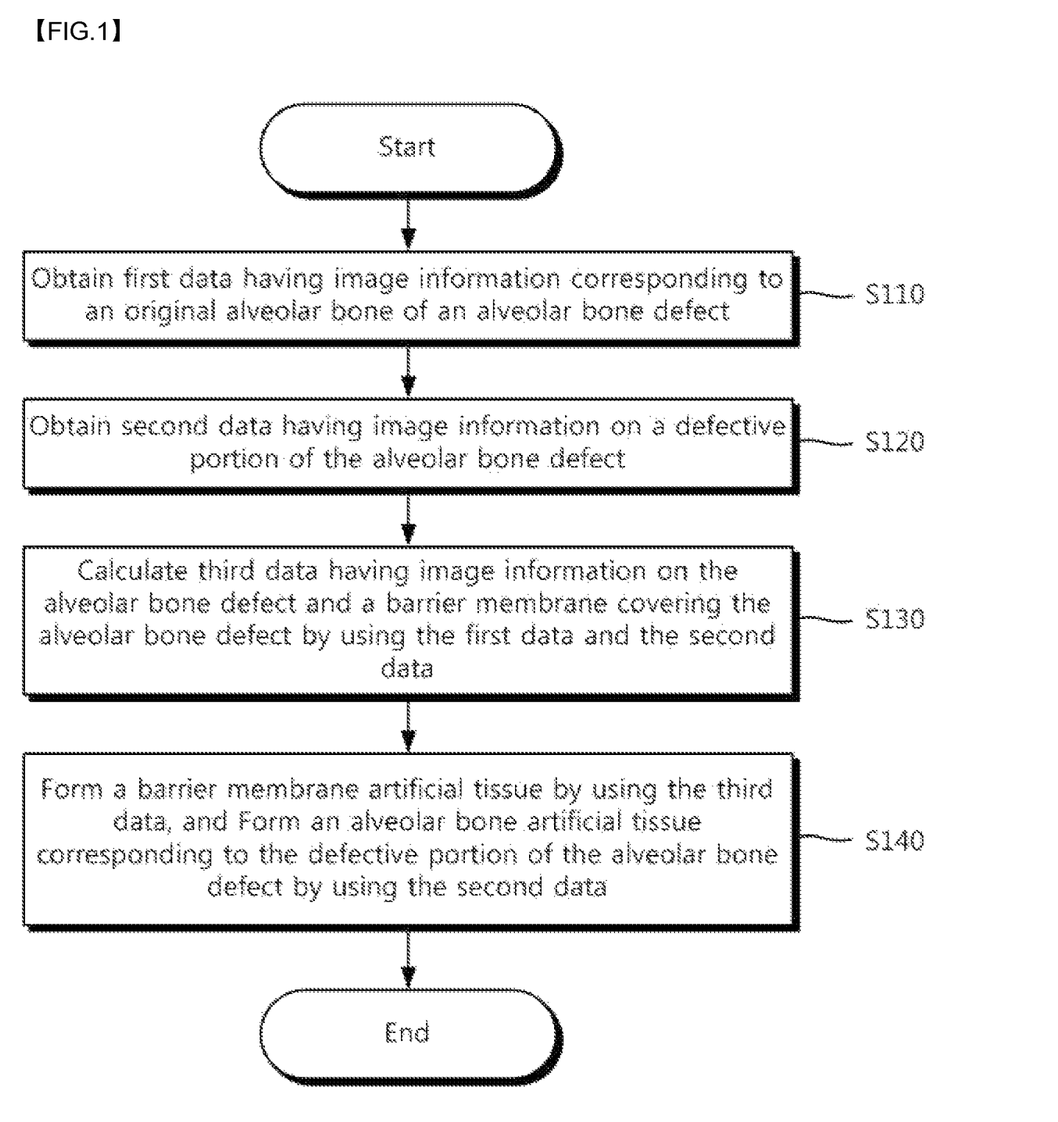
FIG. 1 is a flowchart illustrating a method of forming a customized alveolar bone tissue, according to some embodiments of the inventive concepts.
Figure 2:
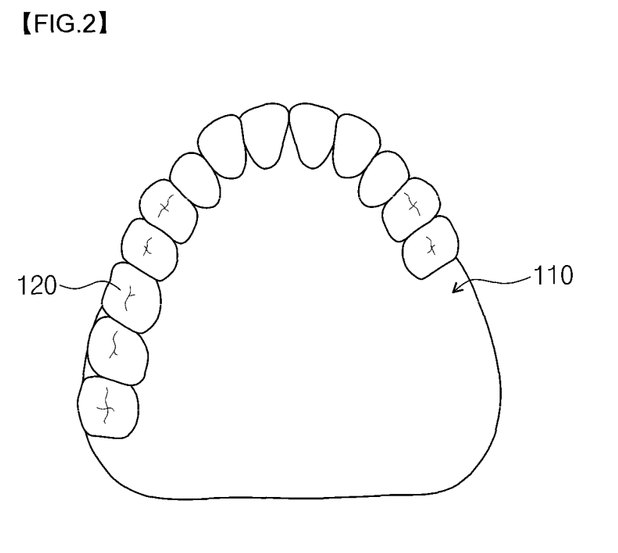
FIGS. 2 and 3 are schematic views illustrating a method of forming a customized alveolar bone tissue according to some embodiments of the inventive concepts.
Figure 3:
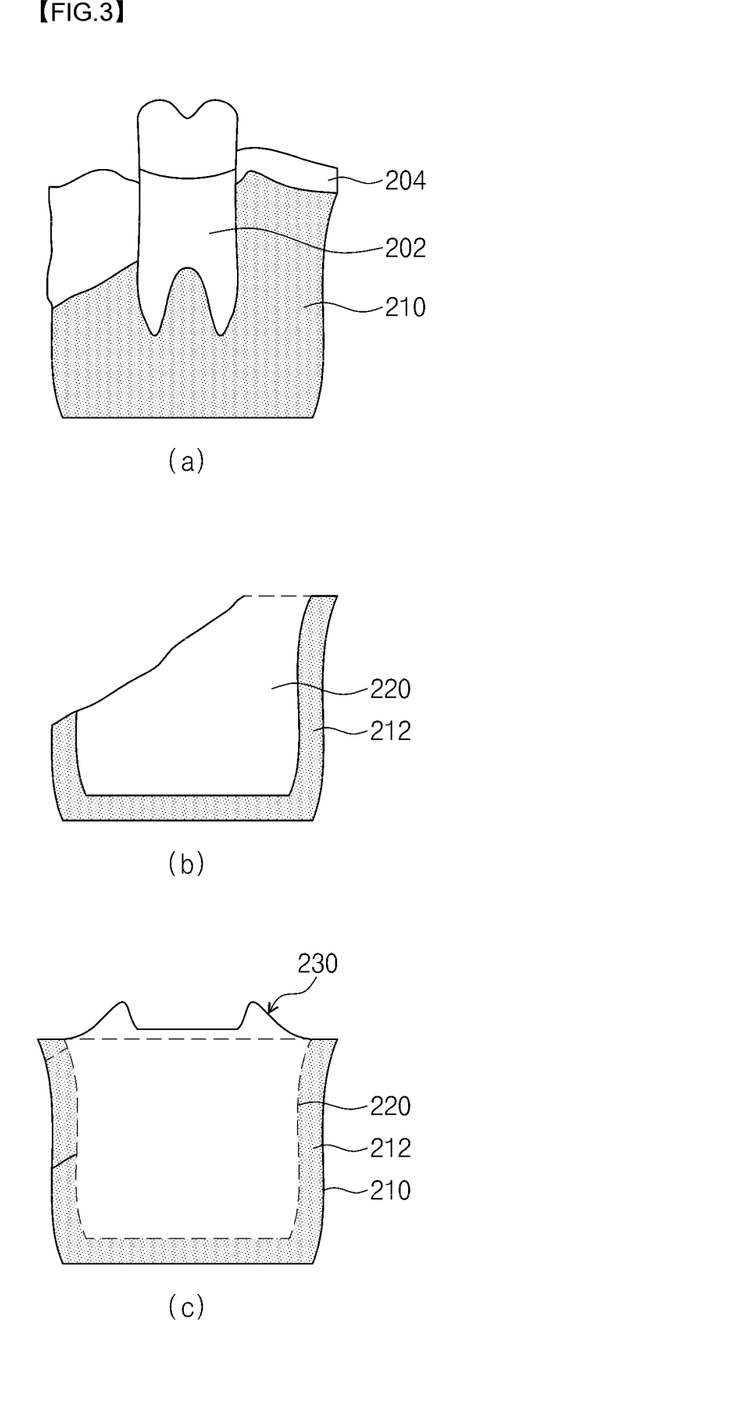

FIG. 1 is a flowchart illustrating a method of forming a customized alveolar bone tissue, according to some embodiments of the inventive concepts. FIGS. 2 and 3 are schematic views illustrating a method of forming a customized alveolar bone tissue according to some embodiments of the inventive concepts.

Referring to FIGS. 1 to 3, in a structure (see a reference designator (a) of FIG. 3) including an original alveolar bone 210, in which a tooth 202 is inserted, and a gum 204 covering the original alveolar bone 210, the tooth 202 and the original alveolar bone 210 may be lost to generate an alveolar bone defect 110 illustrated in FIG. 2. In this case, first data having image information corresponding to the original alveolar bone 210 of the alveolar bone defect 110 may be obtained (S100).

Symmetrical teeth may have the same or similar alveolar bone structure. Thus, according to some embodiments, the image information corresponding to the original alveolar bone 210 of the alveolar bone defect 110 may be obtained using an alveolar bone of a tooth 120 symmetrical to the lost tooth of the alveolar bone defect 110.

In addition, teeth and alveolar bone structures of people of the same race may be the same or similar as each other. Thus, according to other embodiments, the image information corresponding to the original alveolar bone 210 of the alveolar bone defect 110 may be obtained using a standard template alveolar bone of a race to which a patient having the alveolar bone defect 110 belongs.

Second data having image information on a defective portion 220 of the alveolar bone defect 110 may be obtained (S120). The second data may be obtained by three-dimensionally scanning the alveolar bone defect 110. For example, the alveolar bone defect 110 may be scanned by three-dimensional computerized tomography (3D CT) to obtain the second data.

When an alveolar bone is partially regenerated or restored in the alveolar bone defect 110, the second data may have image information on a remaining portion except the regenerated or restored alveolar bone. In more detail, a partial alveolar bone 212 may be regenerated or restored in place of the lost original alveolar bone 210, as illustrated in (b) of FIG. 3. In this case, the second data may have the image information on the defective portion 220 obtained by excluding the regenerated or restored alveolar bone 212 from the lost original alveolar bone 210.

According to some embodiments of the inventive concepts, an alveolar bone artificial tissue corresponding to the defective portion 220 of the alveolar bone defect 110 may be formed using the second data. The alveolar bone artificial tissue may be formed by a three-dimensional (3D) printing process using the second data having the image information on the defective portion 220 of the alveolar bone defect 110. The alveolar bone artificial tissue corresponding to the defective portion 220 of the alveolar bone defect 110 may be formed in the form of cancellous bone by using at least one of various biomaterials and may be grafted on the alveolar bone defect 110.

Third data having image information on the alveolar bone defect 110 and a barrier membrane covering the alveolar bone defect 110 may be calculated using the first data and the second data (S130). The third data may be calculated using a difference between the image information corresponding to the original alveolar bone 210 of the alveolar bone defect 110 in the first data and the image information on the defective portion 220 of the alveolar bone defect 110 in the second data.

As described with reference to (a) and (b) of FIG. 3, when the second data have the image information on the defective portion 220, the image information on the barrier membrane having a shape corresponding to a top shape 230 of the original alveolar bone 210 may be calculated using the difference between the image information corresponding to the original alveolar bone 210 of the alveolar bone defect 110 and the image information on the defective portion 220, as illustrated in (c) of FIG. 3.

A barrier membrane artificial tissue corresponding to the barrier membrane covering the alveolar bone defect 110 may be formed using the third data. The barrier membrane artificial tissue may be formed by a 3D printing process using the third data having the image information on the barrier membrane. The barrier membrane artificial tissue may be formed using at least one of various biomaterials and may be grafted on the alveolar bone defect 110.

As described above, the barrier membrane artificial tissue may have the shape corresponding to the top shape 230 of the original alveolar bone 210. Thus, after the barrier membrane artificial tissue covers the alveolar bone defect 110, an alveolar bone having substantially the same shape as the original alveolar bone 210 may be regenerated and/or restored in the alveolar bone defect 110.

According to some embodiments of the inventive concepts, the image information on the barrier membrane covering the alveolar bone defect 110 may be calculated using the image information corresponding to the original alveolar bone 210 of the alveolar bone defect 110 and the image information on the defective portion 220 of the alveolar bone defect 110, and the barrier membrane artificial tissue may be formed using the image information on the barrier membrane. Thus, the alveolar bone having substantially the same shape as the original alveolar bone 210 may be regenerated and/or restored in the alveolar bone defect 110 by using the barrier membrane artificial tissue.

A system for performing the method of forming the customized alveolar bone tissue according to the embodiments of the inventive concepts will be described hereinafter.

Figure 4:
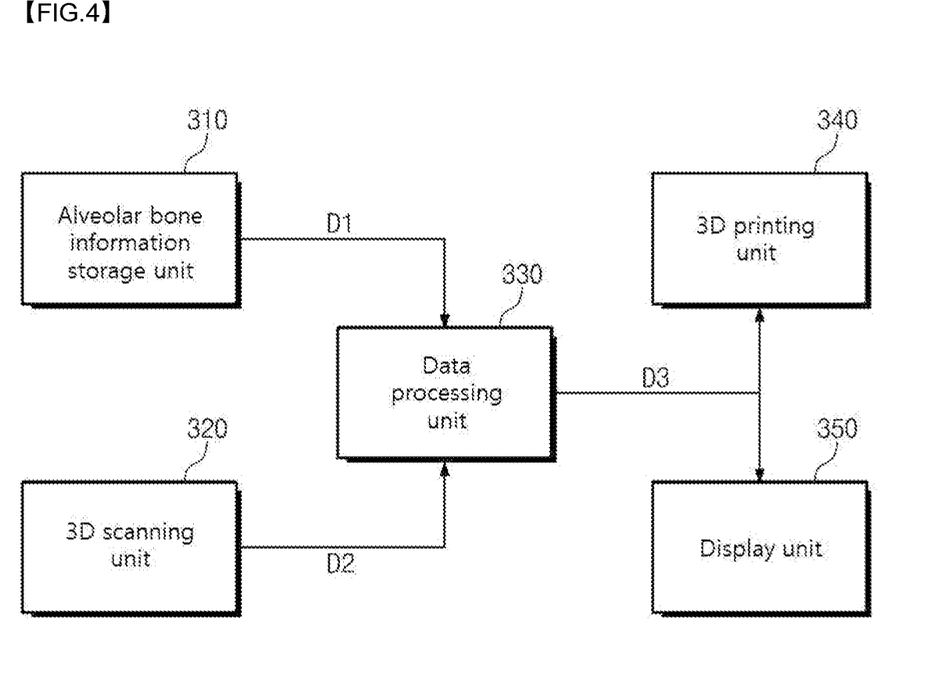
FIG. 4 is a block diagram illustrating a system of forming a customized alveolar bone tissue, according to some embodiments of the inventive concepts.

FIG. 4 is a block diagram illustrating a system of forming a customized alveolar bone tissue, according to some embodiments of the inventive concepts.

Referring to FIG. 4, a system of forming a customized alveolar bone tissue according to some embodiments of the inventive concepts may include an alveolar bone information storage unit 310, a 3D scanning unit 320, a data processing unit 330, a 3D printing unit 340, and a display unit 350.

The alveolar bone information storage unit 310 may store information on an original alveolar bone. The alveolar bone information storage unit 310 may store standard template alveolar bone information on various races. In addition, the alveolar bone information storage unit 310 may store information on an original alveolar bone corresponding to teeth of a patient.

The 3D scanning unit 320 may obtain image information on a defective portion of an alveolar bone defect. The 3D scanning unit 320 may include a 3D CT scanner.

The data processing unit 330 may receive first data D1 having image information corresponding to an original alveolar bone of an alveolar bone defect from the alveolar bone information storage unit 310 and may receive second data D2 having image information on the defective portion of the alveolar bone defect from the 3D scanning unit 320. The first data D1 may include the image information on the original alveolar bone of the alveolar bone defect as described with reference to FIGS. 1 to 3, and the second data D2 may include the image information on the defective portion of the alveolar bone defect as described with reference to FIGS. 1 to 3.

The data processing unit 330 may calculate third data D3, which have image information on a barrier membrane covering the alveolar bone defect, by using the first data D1 and the second data D2. The data processing unit 330 may calculate the third data D3, which have the image information on the barrier membrane having a shape corresponding to a top shape of the original alveolar bone, by using a difference between the image information corresponding to the original alveolar bone of the alveolar bone defect and the image information on the defective portion of the alveolar bone defect, as described with reference to FIGS. 1 to 3.

The data processing unit 330 may transmit the third data D3 to the 3D printing unit 340 and the display unit 350.

The 3D printing unit 340 may receive the third data D3 and may form a barrier membrane artificial tissue corresponding to the barrier membrane by a 3D printing process. In addition, the 3D printing unit 340 may further receive the second data D2 from the 3D scanning unit 320 and may form an alveolar bone artificial tissue corresponding to the defective portion of the alveolar bone defect by a 3D printing process.

The display unit 350 may receive the third data D3 from the data processing unit 330 to display the barrier membrane as an image. In addition, the display unit 350 may further receive the first data D1 and the second data D2 from the alveolar bone information storage unit 310 and the 3D scanning unit 320 to display the original alveolar bone of the alveolar bone defect and the defective portion of the alveolar bone defect as images.

Furthermore, in the embodiment described with reference to FIG. 4, each of the blocks may represent a module, a segment or a portion of a code, which includes one or more executable instructions for executing the specified logical function(s). In addition, in other embodiments, the mentioned functions of the blocks may be performed out of sequence. For example, the functions of two blocks sequentially illustrated may be substantially performed at the same time, and/or the functions of the blocks may sometimes be performed in reverse order.

Figure 5:
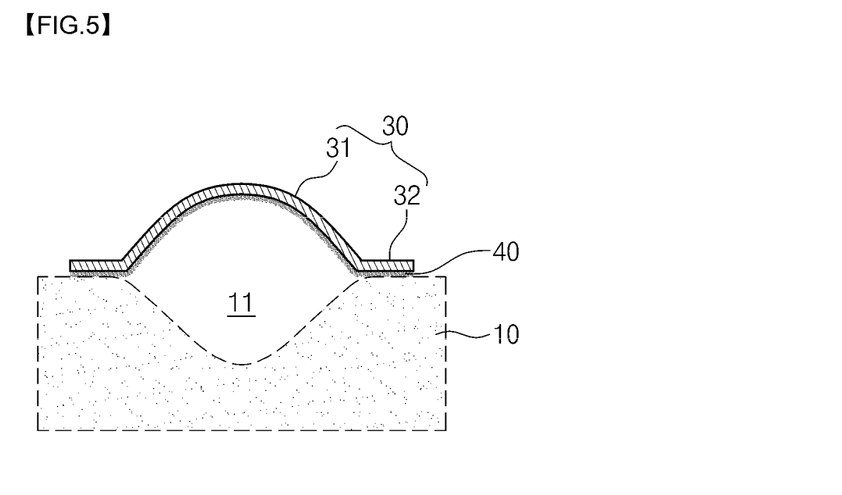
FIG. 5 is a schematic view illustrating a state in which a customized alveolar bone tissue according to an embodiment of the inventive concepts is adhered to an alveolar bone.

FIG. 5 is a schematic view illustrating a state in which a customized alveolar bone tissue according to an embodiment of the inventive concepts is adhered to an alveolar bone.

Referring to FIG. 5, a customized alveolar bone tissue 30 may be adhered to an alveolar bone 10 around an alveolar bone loss region 11 to cover or shield the alveolar bone loss region 11. The customized alveolar bone tissue 11 may be formed of at least one of various biomaterials such as metal (e.g., titanium, nickel, niobium, tantalum, cobalt, and/or chromium), polymer (e.g., PMMA, Nylon, silicones, and/or Teflon), ceramic (e.g., aluminum oxide carbon and/or hydroxyapatite), and a composite material (e.g., carbon-carbon and/or carbon-titanium). The customized alveolar bone tissue 30 includes a cover portion 31 and an adhesion portion 32.

The cover portion 31 may be a portion covering a top of the alveolar bone loss region 11, and the adhesion portion 32 may be a portion that extends from an end of the cover portion 31 and is adhered to the alveolar bone 10 in a region adjacent to the alveolar bone loss region 11. In the present embodiment, the cover portion 31 may have a round shape. However, embodiments of the inventive concepts are not limited thereto. In certain embodiments, the shape of the cover portion 31 may be variously modified. The shape of the cover portion 31 may be changed depending on a shape of the alveolar bone loss region 11 obtained by a CT scan.

An adhesive 40 may be provided between the adhesion portion 32 and the alveolar bone 10 to adhere the adhesion portion 32 to the alveolar bone 10.

As time passes in a state in which the customized alveolar bone tissue 30 is adhered to the alveolar bone 10, fibroblast or fiber forming cells may be grown on and not be in grown in the customized alveolar bone tissue 30 and osteoblast or bone forming cells 10 may be grown in the alveolar bone loss region 11. As a result, the alveolar bone loss region 11 may be reconstructed.

Figure 6:
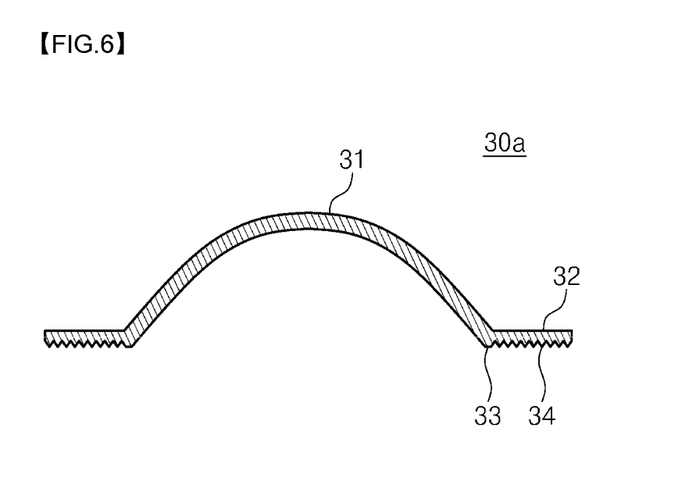
FIGS. 6 to 8 are schematic views illustrating customized alveolar bone tissues according to other embodiments of the inventive concepts.
Figure 7:
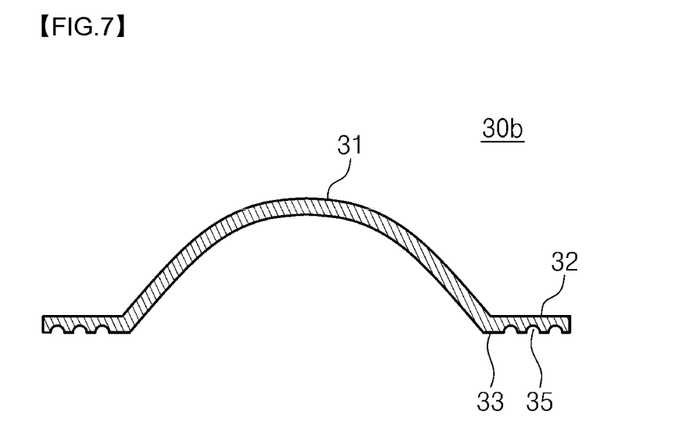
Figure 8:
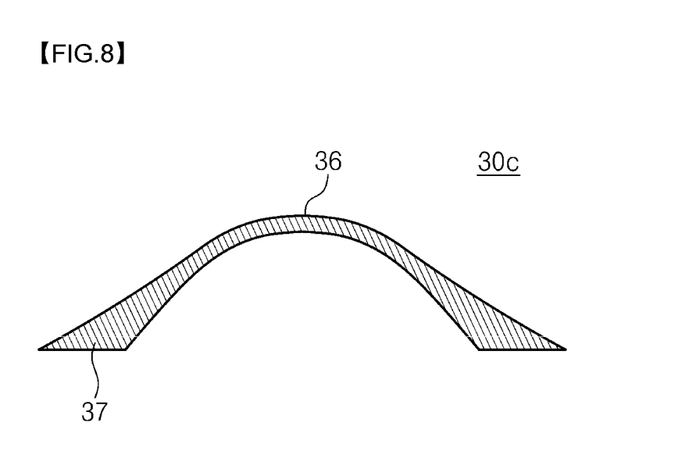

FIGS. 6 to 8 are schematic views illustrating customized alveolar bone tissues according to other embodiments of the inventive concepts.

Referring to FIG. 6, an uneven portion 34 may be formed on an adhesion surface 33 of an adhesion portion 32 of a customized alveolar bone tissue 30a. A roughness of the adhesion surface 33 may be increased by the formation of the uneven portion 34. Since a roughness of a surface of the alveolar bone 10 is generally great, frictional force between the alveolar bone 10 and the adhesion surface 33 may be increased due to the uneven portion 34. The adhesion portion 32 may be stably fixed on the alveolar bone 10 by the increased frictional force without sliding.

In addition, the uneven portion 34 may increase a surface area of the adhesion surface 33, and thus the customized alveolar bone tissue 30a may be stably adhered to the alveolar bone 10 by the adhesive.

Referring to FIG. 7, a receiving groove 35 may be formed in an adhesion surface 33 of an adhesion portion 32 of a customized alveolar bone tissue 30b. The receiving groove 35 may be recessed from the adhesion surface 33 into the adhesion portion 32. The receiving groove 35 may be filled with the tissue adhesive 40, and thus the customized alveolar bone tissue 30 may be stably adhered to the alveolar bone 10.

Referring to FIG. 8, a thickness of a customized alveolar bone tissue 30c may become progressively less from an adhesion portion 37 toward a cover portion 36. In each of the customized alveolar bone tissues 30, 30a and 30b of FIGS. 5 to 7, a degree of bending of a connection portion between the cover portion 31 and the adhesion portion 32 may be great by the shape of the cover portion 31. These shapes of the connection portions may reduce durability of the customized alveolar bone tissues 30, 30a and 30b when external force is continuously applied to the cover portion 31. However, since the customized alveolar bone tissue 30c according to the present embodiment has the thickness becoming progressively less from the adhesion portion 37 toward the cover portion 36, the adhesion portion 37 may stably support the cover portion 36 even though external force is applied to the cover portion 36. Even though not shown in the drawings, the uneven portion or receiving groove described above may be formed at an adhesion surface of the adhesion portion 37.

Figure 9:
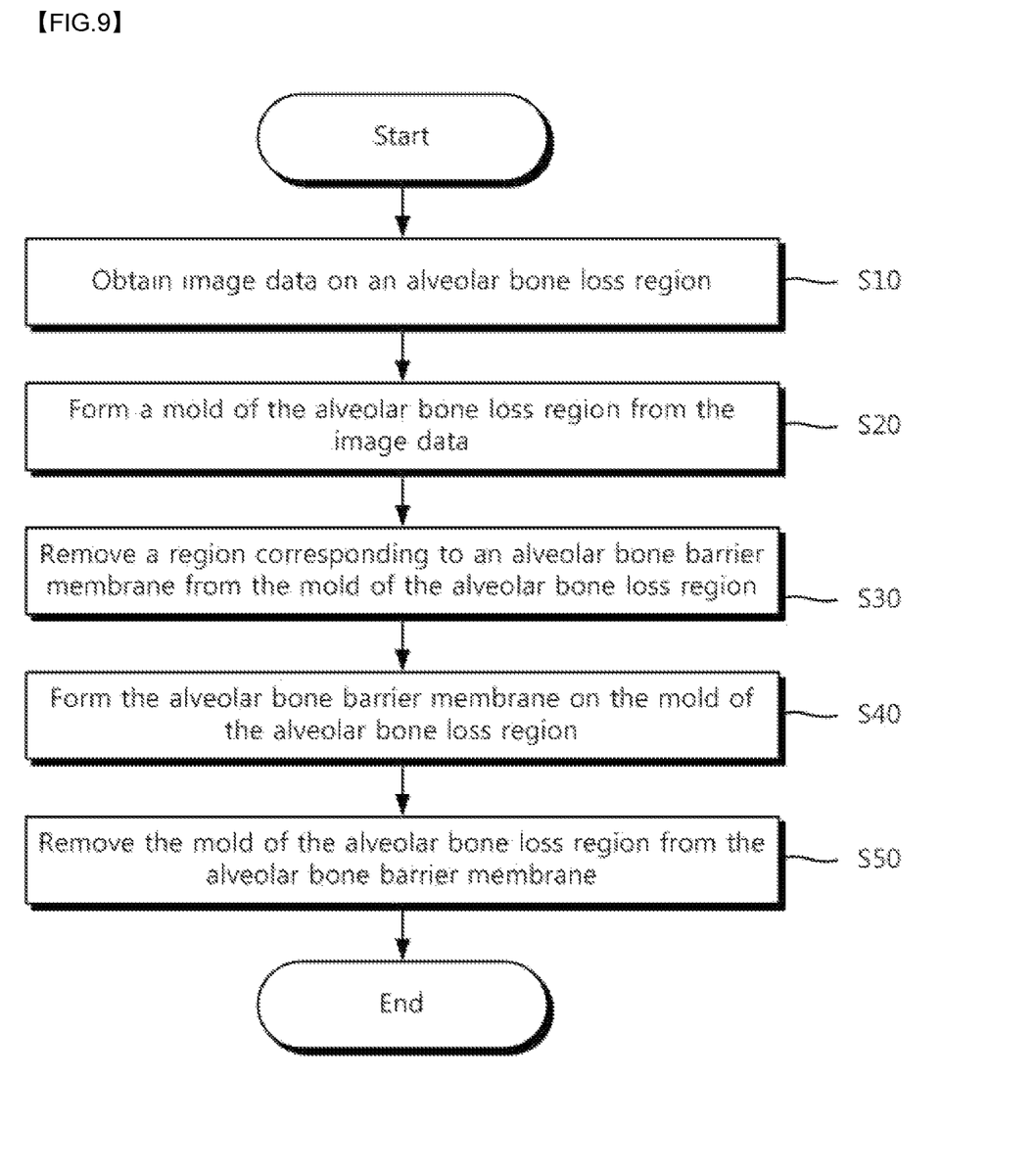
FIG. 9 is a flowchart illustrating a method of forming a customized alveolar bone tissue, according to other embodiments of the inventive concepts.

FIG. 9 is a flowchart illustrating a method of forming a customized alveolar bone tissue, according to other embodiments of the inventive concepts. FIGS. 10 to 14 are schematic views illustrating the method of forming the customized alveolar bone tissue of FIG. 9.

Figure 10:
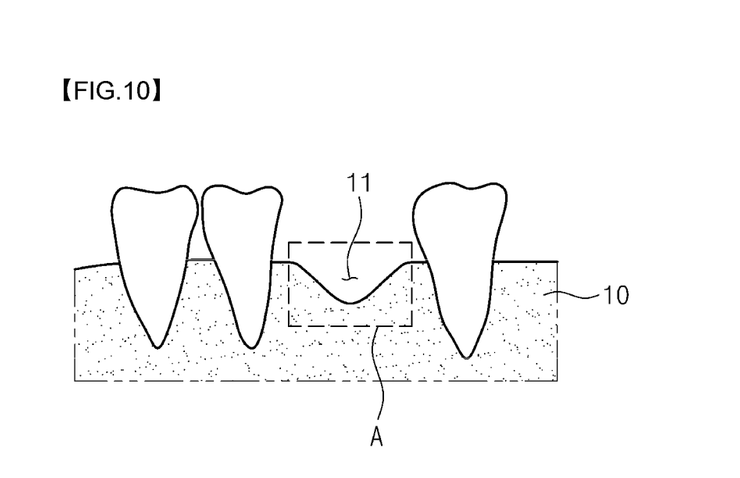
FIGS. 10 to 14 are schematic views illustrating the method of forming the customized alveolar bone tissue of FIG. 9.

Referring to FIGS. 9 to 14, a method of forming a customized alveolar bone tissue may provide a method of forming a customized alveolar bone tissue shielding the alveolar bone loss region 11. As illustrated in FIG. 10, a loss of the alveolar bone may occur by various causes after extraction of a tooth. A method of shielding the alveolar bone loss region 11 by an alveolar bone barrier membrane (or an alveolar bone shielding membrane) may be used for reconstruction of the alveolar bone.

The method of forming the customized alveolar bone tissue according to the inventive concepts may include obtaining image data on the alveolar bone loss region 11 through a CT scan (S10), forming a mold 20 of the alveolar bone loss region 11 from the image data (S20), removing a region 21 corresponding to the customized alveolar bone tissue (i.e., an alveolar bone barrier membrane) from the mold 20 (S30), forming the customized alveolar bone tissue 30 on a mold 20' from which the region 21 corresponding to the customized alveolar bone tissue is removed (S40), and removing the mold 20' from the customized alveolar bone tissue 30 (S50).

In the step S10 of obtaining the image data on the alveolar bone loss region 11 through the CT scan, the alveolar bone 10 of a patient may be scanned through the CT scan to obtain 3D image data of the alveolar bone 10.

Figure 11:
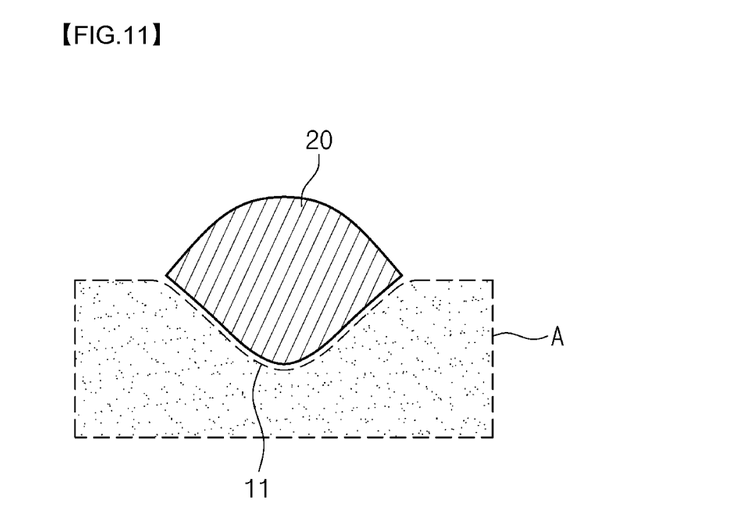

In the step S20 of forming the mold 20 of the alveolar bone loss region 11 from the image data, a 3D image of the alveolar bone loss region 11 may be formed using the image data and the mold 20 may be formed using the 3D image. The mold 20 may be formed using the 3D image through a 3D printing process. FIG. 11 illustrates the mold 20 formed depending on the shape of the alveolar bone loss region 11, according to the embodiments of the inventive concepts.

Figure 12:
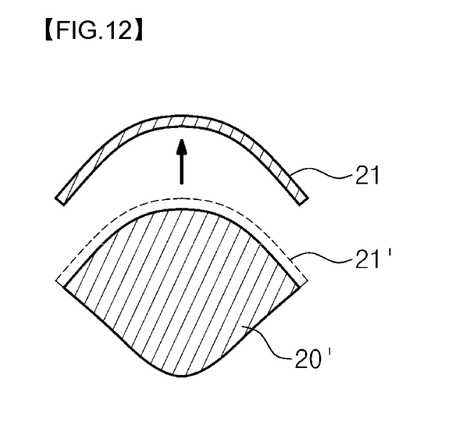

In the step S30 of removing the region 21 corresponding to the customized alveolar bone tissue from the mold 20, the shape of the customized alveolar bone tissue 30 may be predicted or determined, and the region 21 corresponding to the customized alveolar bone tissue 30 may be removed from the mold 20. Since the customized alveolar bone tissue 30 shields or covers a top of the alveolar bone loss region 11, an upper region 21 of the mold 20 may be removed as illustrated in FIG. 12.

In the step S40 of forming the customized alveolar bone tissue 30 on the mold 20' from which the region 21 corresponding to the customized alveolar bone tissue is removed, a material of the customized alveolar bone tissue 30 may be deposited and hardened in a removed region 21' of the mold 20' to form the customized alveolar bone tissue 30. According to an embodiment, the material of the customized alveolar bone tissue 30 may include a biomaterial which can be outputted through a 3D printer. Alternatively, the material of the customized alveolar bone tissue 30 may include a biomaterial which is not easily outputted through the 3D printer. The customized alveolar bone tissue 30 may be coated in a resin state on the mold 20'.

Figure 13:
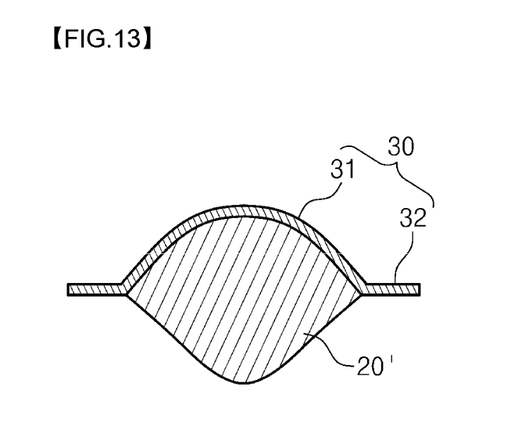

The customized alveolar bone tissue 30 formed at the mold 20' may include a cover portion 31 and an adhesion portion 32. The cover portion 31 may be a portion which is deposited in the removed region 21' of the mold, and the adhesion portion 32 may be a portion which extends from the cover portion 31. As illustrated in FIG. 13, when the customized alveolar bone tissue 30 shields the alveolar bone loss region 11, the cover portion 31 may cover a top of the alveolar bone loss region 11, and the adhesion portion 32 may be adhered to the alveolar bone 10 in a region adjacent to the alveolar bone loss region 11.

Figure 14:
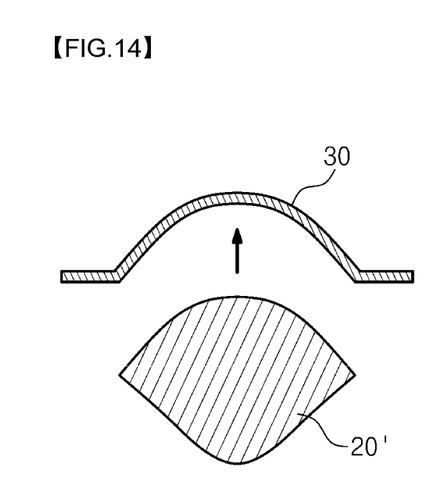

In the step S50 of removing the mold 20' from the customized alveolar bone tissue 30, the customized alveolar bone tissue 30 may be separated from the mold 20' as illustrated in FIG. 14.

In another embodiment, the method of forming a customized alveolar bone tissue may further include forming the uneven portion 34 at the adhesion surface 33 of the adhesion portion 32, as illustrated in FIG. 6. A roughness of the adhesion surface 33 may be increased by the formation of the uneven portion 34. Since a roughness of a surface of the alveolar bone 10 is generally great, frictional force between the alveolar bone 10 and the adhesion surface 33 may be increased due to the uneven portion 34. The adhesion portion 32 may be stably fixed on the alveolar bone 10 by the increased frictional force without sliding.

In addition, the uneven portion 34 may increase a surface area of the adhesion surface 33, and thus the customized alveolar bone tissue 30a may be stably adhered to the alveolar bone 10 by the adhesive 40 of FIG. 5.

In still another embodiment, the method of forming a customized alveolar bone tissue may further include forming the receiving groove 35 at the adhesion surface 33 of the adhesion portion 32, as illustrated in FIG. 7. The receiving groove 35 may be recessed from the adhesion surface 33 into the adhesion portion 32. When the customized alveolar bone tissue 30 is adhered to the alveolar bone 10 by the adhesive 40, the receiving groove 35 may be filled with the adhesive 40, and thus the customized alveolar bone tissue 30 may be stably adhered to the alveolar bone 10.

In yet another embodiment of the inventive concepts, the customized alveolar bone tissue 30c of which the thickness becomes progressively less from the adhesion portion 37 toward the cover portion 36 like FIG. 8 may be formed in the step S40 of forming the customized alveolar bone tissue 30 on the mold 20' from which the region 21 corresponding to the customized alveolar bone tissue is removed. In each of the customized alveolar bone tissues 30, 30a and 30b of FIGS. 5 to 7, a degree of bending of a connection portion between the cover portion 31 and the adhesion portion 32 may be great by the shape of the cover portion 31. These shapes of the connection portions may reduce durability of the customized alveolar bone tissues 30, 30a and 30b when external force is continuously applied to the cover portion 31. However, since the customized alveolar bone tissue 30c according to the present embodiment has the thickness becoming progressively less from the adhesion portion 37 toward the cover portion 36, the adhesion portion 37 may stably support the cover portion 36 even though external force is applied to the cover portion 36. Even though not shown in the drawings, the uneven portion or receiving groove described above may be formed at an adhesion surface of the adhesion portion 37.

The customized alveolar bone tissues and the methods of forming the same according to the embodiments of the inventive concepts may be used in the treatments for reconstruction of the alveolar bone defect or the alveolar bone loss region.

According to some embodiments of the inventive concepts, the image information on the barrier membrane artificial tissue and the alveolar bone artificial tissue for compensating the alveolar bone defect may be calculated using the image information corresponding to the original alveolar bone of the alveolar bone defect and the image information on the defective portion of the alveolar bone defect. The alveolar bone artificial tissue and the barrier membrane artificial tissue capable of easily regenerating and/or restoring the alveolar bone which is substantially the same as the original alveolar bone may be formed by the 3D printing processes using the image information on the alveolar bone artificial tissue and the barrier membrane artificial tissue. Thus, it is possible to provide the customized alveolar bone tissue and the method of forming the same, which reduce an operation time of the alveolar bone graft and easily restore a functional and aesthetic tooth.

In addition, according to some embodiments of the inventive concepts, it is possible to provide the customized alveolar bone tissue meeting an alveolar bone shape of a patient, and the method of forming the same.

Moreover, according to some embodiments of the inventive concepts, it is possible to provide the customized alveolar bone tissue and the method of forming the same, which can reconstruct the functional and aesthetic alveolar bone that has a similar shape to the original alveolar bone in a healthy condition.

Furthermore, according to some embodiments of the inventive concepts, it is possible to provide the customized alveolar bone tissue and the method of forming the same, which reduce the operation time and prevent damage of a surrounding bone tissue.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. A method of forming a customized alveolar artificial bone tissue for shielding an alveolar bone loss region, the method comprising:
   obtaining image data on the alveolar bone loss region through a computerized tomography (CT) scan;
   forming a mold of the alveolar bone loss region from the image data;
   removing a region corresponding to the customized alveolar artificial bone tissue from the mold;
   forming the customized alveolar artificial bone tissue on the mold from which the region corresponding to the customized alveolar artificial bone tissue is removed; and
   removing the mold from the customized alveolar artificial bone tissue, wherein the forming of the customized alveolar artificial bone tissue comprises:
   forming a cover portion in an empty region formed by the removing of the region corresponding to the customized alveolar artificial bone tissue from the mold; and
   forming an adhesion portion extending flat from an end of the cover portion,
   wherein the forming of the customized alveolar artificial bone tissue comprises depositing a material of the customized alveolar artificial bone tissue on the mold from which the region corresponding to the customized alveolar artificial bone tissue is removed,
   wherein a thickness of the customized alveolar artificial bone tissue becomes smaller from the adhesion portion toward the cover portion,
   wherein the adhesion portion comprises an adhesion surface configured to adhere to an alveolar bone in a region adjacent to the alveolar bone loss region by an adhesive,
   wherein the adhesion surface has a max thickness of the customized alveolar artificial bone tissue, and
   wherein the adhesion surface has an uneven portion or a receiving groove which is recessed from the adhesion surface and has a closed upper region such that the uneven portion or the receiving groove is filled with the adhesive.

2. The method of claim 1, wherein the obtaining of the image data comprises: obtaining a three-dimensional (3D) image data on the alveolar bone loss region, and wherein the forming of the mold comprises: forming the mold by a 3D printer using the 3D image data.

3. The method of claim 1, wherein the forming of the customized alveolar artificial bone tissue further comprises: hardening the material of the customized alveolar artificial bone tissue to form the customized alveolar artificial bone tissue.

4. The method of claim 3, wherein the material of the customized alveolar artificial bone tissue comprises a biomaterial or a resin.

\* \* \* \* \*